US008865457B2

(12) United States Patent
Polaniec et al.

(10) Patent No.: US 8,865,457 B2
(45) Date of Patent: Oct. 21, 2014

(54) ACTIVE, MICRO-WELL THERMAL CONTROL SUBSYSTEM

(75) Inventors: Jim Polaniec, Avon, OH (US); David J. Lapeus, Medina, OH (US); Tim Greszler, Oberlin, OH (US); Frank Klingshirn, Medina, OH (US); Chris Sturges, Amherst, OH (US); Matt Schmidt, Strongsville, OH (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 487 days.

(21) Appl. No.: 12/077,193

(22) Filed: Mar. 17, 2008

(65) Prior Publication Data

US 2008/0227186 A1 Sep. 18, 2008

Related U.S. Application Data

(60) Provisional application No. 60/918,190, filed on Mar. 15, 2007.

(51) Int. Cl.
*C12M 1/02* (2006.01)
*B01L 7/00* (2006.01)

(52) U.S. Cl.
CPC ............ *B01L 7/52* (2013.01); *B01L 2200/147* (2013.01); *B01L 2300/1844* (2013.01); *B01L 2300/1822* (2013.01); *B01L 2300/185* (2013.01); *B01L 2300/0829* (2013.01)
USPC ............ 435/287.2; 435/6.1; 422/38; 422/109

(58) Field of Classification Search
CPC ................ B01L 7/52; B01L 2200/147; B01L 2300/0829; B01L 2300/185; B01L 2300/1822; B01L 2300/1844
USPC ..................................... 435/6, 287.2; 422/38
See application file for complete search history.

(56) References Cited

U.S. PATENT DOCUMENTS

| | | | | |
|---|---|---|---|---|
| 5,602,756 | A | 2/1997 | Atwood et al. | |
| 5,939,312 | A | 8/1999 | Baier et al. | |
| 6,153,426 | A | 11/2000 | Heimberg | |
| 6,306,658 | B1 * | 10/2001 | Turner et al. | 436/37 |
| 6,556,940 | B1 | 4/2003 | Tretiakov et al. | |
| 7,060,948 | B2 | 6/2006 | Cho et al. | |
| 2002/0072112 | A1 * | 6/2002 | Atwood et al. | 435/303.1 |
| 2002/0100582 | A1 * | 8/2002 | Oldenburg | 165/253 |
| 2004/0223885 | A1 * | 11/2004 | Keen et al. | 422/99 |
| 2004/0258568 | A1 * | 12/2004 | Lurz et al. | 422/99 |

* cited by examiner

*Primary Examiner* — Michael Hobbs

(57) ABSTRACT

Devices and systems for active thermal control of sample holding devices for bDNA testing, polymerase chain reaction testing, chemiluminescent immuno-assay testing, and so forth. The thermal control subsystem includes a fluidic circuit, first and second heater assemblies, a centrifugal pump, and a heat exchange device. The first and second heater assemblies include a heat removal device and a controllable thermo-electric device. One or both of the heater assemblies can include a heat spreader. A controller actively controls the pump, the heat removal device, and the thermo-electric devices, to thermally-control sample-containing vessels retained in the holding device.

15 Claims, 2 Drawing Sheets

ACTIVE, MICRO-WELL THERMAL CONTROL SUBSYSTEM

CROSS REFERENCE TO RELATED APPLICATIONS

Pursuant to 35 U.S.C. §119(e), a right of priority to U.S. Provisional Patent Application No. 60/918,190 filed on Mar. 15, 2007 and entitled "Active, Micro-well Thermal Control Subsystem" is asserted.

STATEMENT REGARDING FEDERALLY SPONSORED RESEARCH OR DEVELOPMENT (Not Applicable)

BACKGROUND OF THE INVENTION

The present invention relates to devices and systems for providing active thermal control of sample-containing assay trays and, more specifically, to devices and systems that provide improved, uniform heat transfer from a sample-containing assay tray using thermo-electric devices, heat spreader plates, and liquid heat exchangers.

Protocols for amplification of RNA or DNA, for example, during polymerase chain reaction (PCR), bDNA, and similar testing, require rapid and uniform heating and cooling of a plurality of sample-containing vessels. Because such testing typically is performed in batches, the rapid and uniform heating and cooling are applied to the plurality of sample-containing vessels simultaneously.

Conventionally, heat transfer for thermo-electric devices and/or heating elements is accomplished by conduction, while cooling of thermal system components is done by convection, or, more conventionally, by air convection. However, thermal performance of such systems is limited by the space needs of relatively large thermal components.

Therefore, it would be desirable to provide a liquid heat-transferring concept that transfers heat by liquid convection rather than by air convection to improve heat transfer and to provide a more compact thermal component size. Thermal control of sensitive reagents used in these protocols is also highly desirable.

SUMMARY OF THE INVENTION

An active thermal control subsystem for controlling the temperature of a sample-containing holding device used in connection with bDNA testing, polymerase chain reaction testing, chemiluminescent immuno-assay testing, and the like is disclosed. The thermal control subsystem includes first and second assemblies, a pump, and a heat exchange device that are fluidly-coupled via a fluidic circuit.

The first and second assemblies include a heat removal device and a thermo-electric device(s). One or more of the first and the second assemblies includes a heat spreader. The heat spreader is further thermally-coupled to the sample-containing holding device, such as a micro-well assay tray. The thermo-electric device(s) is/are disposed between the heat removal device and the heat spreader. Current transmitted to the thermo-electric device(s) is controlled. Depending on the voltage at each junction, heat can be transferred bi-directionally, either from the heat spreader to the heat removal device or from the heat removal device to the heat spreader.

A testing system having active thermal control of a sample-holding device and/or a reagent-containing device is also disclosed. The system includes the thermal control subsystem described above and a controller. The controller controls operation of the pump, the heat exchange device, and the thermo-electric device(s) associated with the first and second assemblies to control the temperature of the sample-holding device and/or reagent-containing device.

Optionally, the system can include a holding device for retaining reagent-containing vessels that is fluidly-coupled to the fluidic system and/or a drain line that is fluidly-coupled to the fluidic system for removing heat-transferring fluid.

BRIEF DESCRIPTION OF THE DRAWINGS

The invention will be better understood by reference to the following more detailed description and accompanying drawings where like reference numbers refer to like parts.

DETAILED DESCRIPTION OF THE INVENTION

U.S. Provisional Patent Application No. 60/918,190 filed on Mar. 15, 2007 and entitled "Active, Micro-well Thermal Control Subsystem", from which priority is claimed, is incorporated herein by reference.

Figure 1:
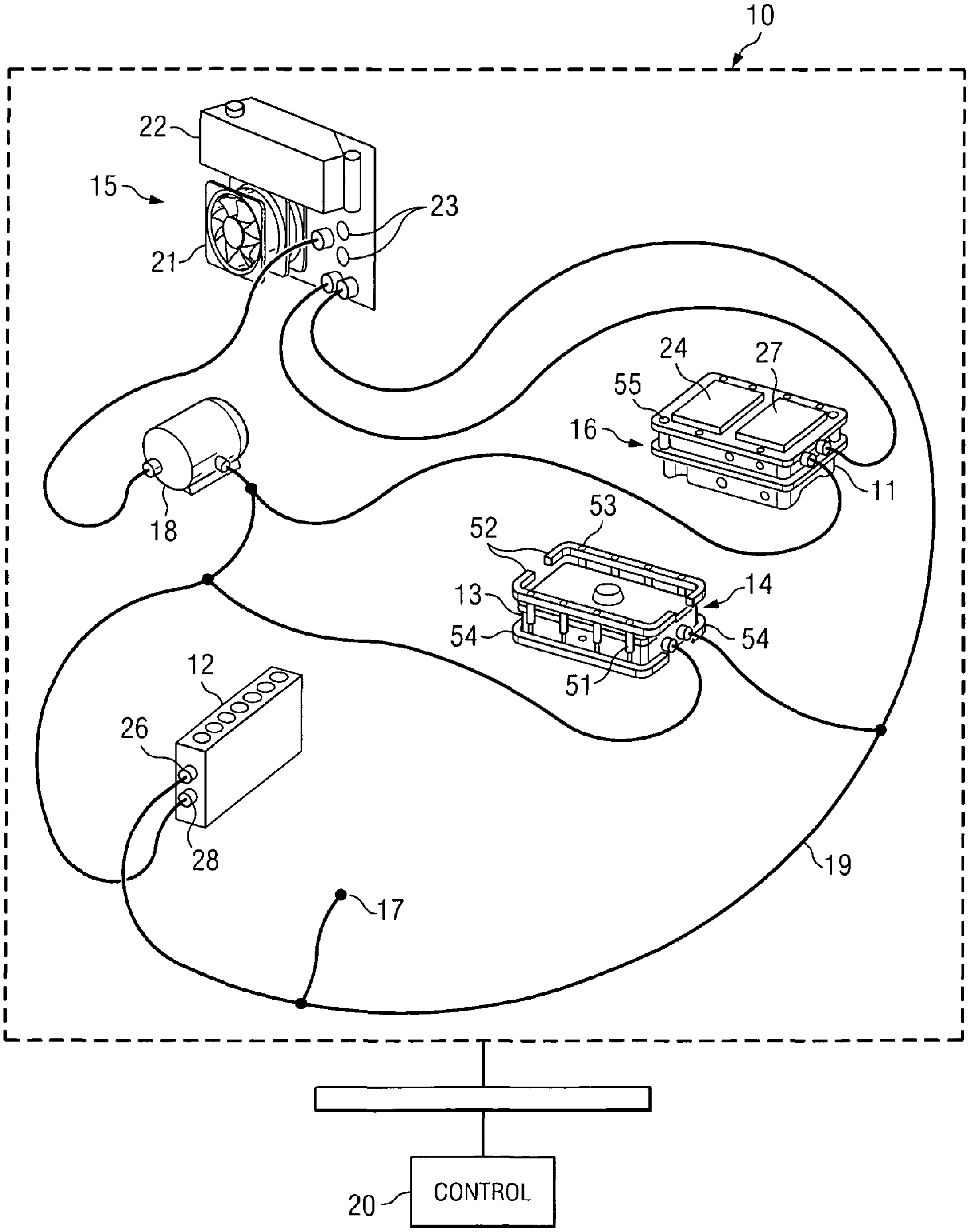
FIG. 1 shows a diagram of a well subsystem in accordance with the present invention.

An active control, micro-well thermal breadboard/micro-well thermal subsystem, e.g., for a bDNA testing system, a chemiluminescent immunoassay system, a PCR testing system, and the like, is disclosed. Referring to FIG. 1, there is shown an active thermal control subsystem 10 for controlling the temperature of at least one micro-well assay tray (not shown). The micro-well assay tray discussed in this disclosure corresponds to a conventional micro-well titer plate for holding multiple, i.e., 96, sample-containing cuvettes. The invention, however, is applicable to other sample-holding devices.

The subsystem 10 is structured and arranged to maintain micro-well plate incubation temperatures between about 20 degrees Centigrade (° C.) and about 70° C., which is to say, between about 68 degrees Fahrenheit (° F.) and 158° F., respectively. Moreover, the subsystem 10 is structured and arranged so that the average temperature of the micro-well assay trays can be maintained within approximately ±0.5° C. of the specified or desired temperature and, moreover, so that the temperature difference between adjacent micro-well assay trays does not exceed approximately ±0.5° C. Optionally, the subsystem 10 of the present invention can also be structured and arranged to control the temperature of sensitive reagents used in the course of the PCR, chemiluminescent or other testing.

The micro-well thermal subsystem 10 of the present invention includes first and second heater trays 14 and 16, a heat exchanger 15, a pump 18, and a fluidic system 19. Optionally, the micro-well thermal subsystem 10 can include a reagent holding device 12 and/or a system controller 20, which in FIG. 1 is shown separate from the micro-well thermal subsystem 10.

Each of the first and second heater trays 14 and 16, the heat exchanger 15, and the reagent holding device 12 are fluidly-coupled via a common fluidic system 19. The fluidic system 19 includes fluid conduits, such as flexible tubing, for circulating a heat-transferring liquid. A drain line 17 can be provided to drain the fluidic system 19 and/or to bleed off excess heat-transferring liquid within the fluidic system 19.

A centrifugal pump 18, such as the RD-05CV24 manufactured by Iwaki Co., Ltd. of Tokyo, Japan, is also fluidly-coupled to the fluidic system 19. The centrifugal pump 18 is adapted to circulate a heat-transferring liquid, such as a water and ethylene-glycol (WEG) mixture, between the first and second heater trays 14 and 16 and the heat exchanger 15, to transfer heat from or transfer heat to the first and second heater trays 14 and 16; between the reagent holding device 12 and the heat exchanger 15, to transfer heat from or transfer heat to the reagent-containing vessels disposed in the reagent holding device 12; and between the fluidic system 19 and a coolant reservoir 25, to add heat-transferring liquid to or to drain heat-transferring liquid from the fluidic system 19.

The reagent holding device 12 of the present invention includes inlet and outlet ports 26 and 28, respectively, and associated internal fluidic connections (not shown) for controlling the temperature of reagent-containing vessels, e.g., test tubes, disposed in the reagent holding device 12. The inlet and outlet ports 26 and 28 are releasably attachable to the external fluidic system 19 for circulating a heat-transferring liquid through the fluidic connections and about the reagent-containing vessels, to control the temperature of the reagent-containing test tubes by liquid convection.

The heat exchanger 15 can be a conventional, radiator-type heat exchanger, having a coolant reservoir 22, a plurality of coils 23, and at least one fan assembly 21. The coolant reservoir 22 is adapted to hold heat-transferring liquid that has been heated in the first or second heater trays 14 and 16 and elsewhere in the fluidic system 19 temporarily. The plurality of coils 23 is adapted to circulate heat-transferring liquid from the coolant reservoir 22 to the fluidic system 19. The fan assembly(ies) 21 is/are adapted to move ambient air against and around the coils 23, to remove heat from the heat-transferring liquid circulating therein. Once sufficient heat has been removed from the heat-transferring liquid circulating in the coils 23, the heat-transferring liquid is re-circulated to the first and second heater trays 14 and 16, to the reagent holding device 12, and/or to the coolant reservoir 22.

Figure 2:
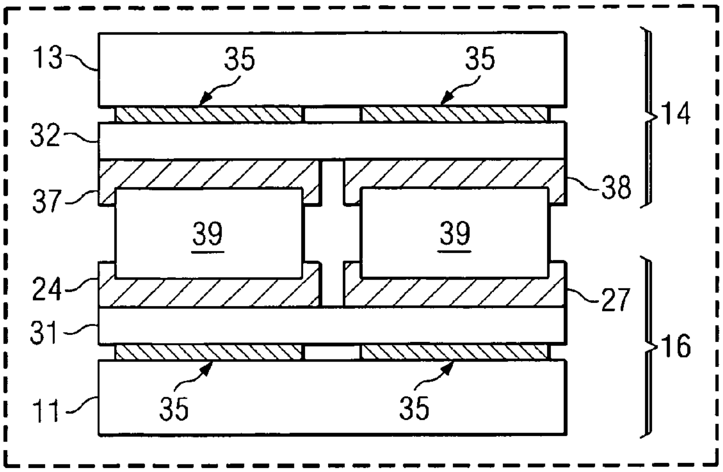
FIG. 2 shows a diagram of micro-well assay trays disposed between first and second heater plates in accordance with the present invention.

Referring to FIG. 2, a first side of each of the first and second heater trays 14 and 16 is operationally- and thermally-coupled to the item(s) being thermally-controlled, e.g., at least one 96-position micro-well assay tray 39. The first side of the second heater tray 16 shown in FIG. 1 and FIG. 2 includes two sub-portions 24 and 27, each of which is adapted for holding a conventional, 96-position micro-well titer plate 39. The first side of the first heater tray 14 includes two sealing pads 37 and 38 that are also adapted, in combination with the associated sub-portions 24 and 27 of the second heater tray 16, for securing the 96-position micro-well titer plates 39 therebetween.

As shown in FIG. 2, the sub-portions 24 and 27 of the second heater plate 16 are thermally-coupled to a heat spreader 31. Optionally (as shown in FIG. 2), the sealing pads 37 and 38 of the first heater tray 14 also can be thermally-coupled to a heat spreader 32. Experimentation by the inventors evinced that micro-well thermal performance is more greatly influenced by the second (lower) heater tray 16 than by the first (upper) heater tray 14. Hence, a heat spreader 32 for the first (upper) heater tray 14 can be omitted to reduce cost and simplify design.

The heat spreaders 31 and 32 are adapted to avoid hot or cold spots within the micro-well assay trays 39, especially during rapid, ramp temperature changes. The heat spreaders 31 and 32 also prevent direct heat transfer from thermo-electric devices (TEDs) 35, which are disposed on the opposite sides of the heat spreaders 31 and 32, to the center of the micro-well assay trays 39.

Heat spreaders 31 and 32 can be manufactured of copper, aluminum or some other relatively-highly thermally-conductive material. More specifically, the heat spreaders 31 and 32 are adapted to ensure that each micro-well assay tray 39 is maintained within approximately ±0.5° C. (± about 1° F.) of the specified temperature; that the temperature difference between adjacent micro-well assay trays 39 does not exceed approximately ±0.5° C.; that the ramp temperature change rate, i.e., "ramping", for heating or cooling the micro-well assay trays 39 is between approximately 1° C./minute (about 2° F.) and approximately 10° C./minute (about 18° F./minute) and, more preferably, between approximately 1° C./minute and approximately 7° C./minute (about 13° F./minute); and that, during ramping, the upper (or lower) target temperature is not exceeded by more than approximately 0.5° C.

As mentioned above, one side of each of the heat spreaders 31 and 32 is operationally- and thermally-coupled to a plurality of thermo-electric devices (TED) 35, which are disposed to be in registration with the sub-portions 24 and 27 and the micro-well assay trays 39. TEDs 35 are thermal controllers that transfer heat across their thickness by the Peltier effect. According to the Peltier effect, applying voltage to the junctions of two dissimilar metals causes a temperature difference between the two junctions. Hence, by varying the polarity of the voltages applied to the junctions, temperatures can be increased or decreased and, more importantly, heat can be transferred from one side of the TED 35 to the other side of the TED 35 in either direction.

Advantageously, heat can be transferred from heat removal devices, i.e., heat sinks 11 and 13, respectively, to the heat spreaders 31 and 32, when ramping up the temperature of the micro-well assay trays 39. Alternatively, heat can be transferred from the heat spreaders 31 and 32 to the heat sinks 11 and 13, respectively, when ramping down the temperature of the micro-well assay trays 39.

Figure 3A:
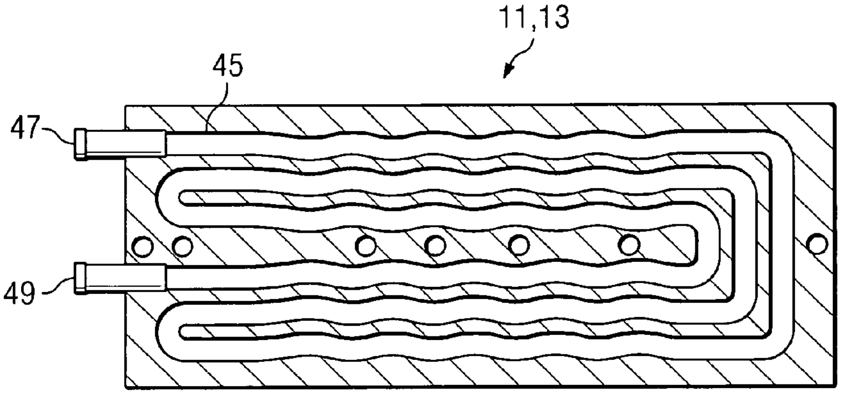
FIG. 3A shows a diagram of a plan view of a heat sink (taken from the bottom) in accordance with the present invention.
Figure 3B:
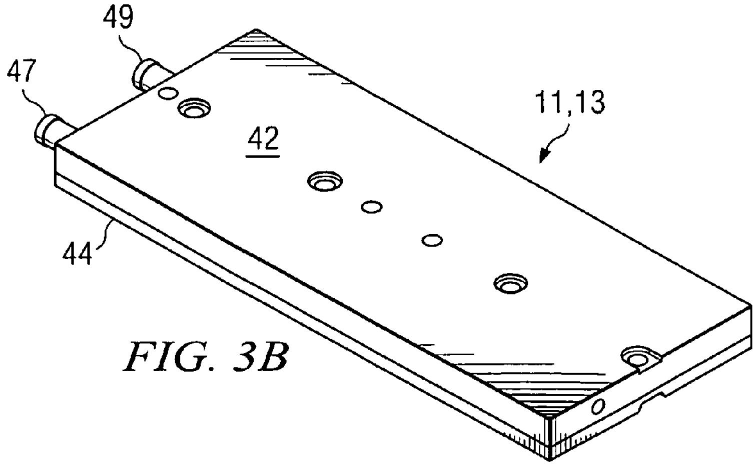
FIG. 3B shows a diagram of an isometric view of the heat sink of FIG. 3A.

Heat sinks 11 and 13 are thermal masses used for removing heat by conduction and/or by convection. Heat sinks 11 and 13 are well known to the art and will not be discussed in great detail. However, referring to FIGS. 3A and 3B, heat sinks 11 and 13 can include two opposing, relatively-highly thermally-conductive plates 42 and 44 that are releasably attachable to one another. At least one fluid-carrying channel 45 is disposed between the two plates 42 and 44. The fluid-carrying channel(s) 45 of the heat sinks 11 and 13 includes an inlet port 49 and an outlet port 47, which are fluidly-coupled to the fluidic system 19.

During operation, the direction of heat transfer between the heat sinks 11 and 13 and the micro-well assay trays 39 depends on whether the TEDs 35 are in a heating or in a cooling mode. During a heating mode, a rapid ramp-up temperature change of the micro-well assay tray(s) 39 is desired. For example, during PCR testing, conventionally, an analyte-containing sample is heated from ambient temperature to about 70° C. (about 158° F.) during the initial de-naturing cycle.

Accordingly, voltages at the junctions of the TEDs 35 are controlled so that heat is transferred from the heat sinks 11 and 13 to the micro-well assay trays 39. More specifically, the heat-transferring liquid in the fluidic system 19 is heated to an elevated temperature (or is allowed to remain at an elevated temperature) sufficient to transfer the necessary heat from the heat-transferring liquid to the heat sink(s) 11 and/or 13. In some instances, the available heat in the heat sink(s) 11 or 13 may be sufficient to rapidly change the temperature of the micro-well assay trays 39 without using a heated liquid to heat the heat sink(s) 11 or 13.

During a cooling mode, a rapid ramp-down temperature change of the micro-well assay tray(s) 39 is desired. Accordingly, voltages at the junctions of the TEDs 35 are controlled so that heat is transferred from the micro-well assay trays 39 to the heat sink(s) 11 and/or 13 via the TEDs 35. Heat-transferring liquid circulating though the channels disposed in the heat sink(s) 11 and/or 13 removes heat from the heat sink(s) 11 and/or 13.

A controller 20 (FIG. 1) is electrically-coupled to the system 10, for the purpose of controlling the centrifugal pump 18, the heat exchanger 15, and each of the TEDs 35 associated with the first and second heater trays 14 and 16. The controller 20 can include electronic hardware, software, and/or applications, driver programs, and other algorithms as well as input/output devices to control the machination of the centrifugal pump 18, the heat exchanger 15, and each of the TEDs 35. More specifically, the controller 20 is adapted to control the temperature of the heat-transferring liquid and, further, to control the heat transfer direction of the TEDs 35, to heat or cool the micro-well assay tray(s) 39 automatically, and in accordance with the protocol of the PCR, bDNA, and related tests.

In one aspect of the present invention, the first heater tray 14 is releasably attachable to the second heater tray 16. Any clamping or other means for temporarily securing the first heater tray 14 to the second heater tray 16 can be used. FIG. 1 shows a fastener-based embodiment, whereby a plurality of fasteners 51, e.g., machine screws, bolts, and the like, are disposed through holes 53 in upper and lower clamping portions 52 and 54, respectively, and, further disposed in associated openings 55 disposed in the second heater tray 16. As the fastening devices 51 are tightened, the upper and lower clamping portions 52 and 54 secure the upper heater tray 14. As the fastening devices 51 are tightened more, the upper and lower heater trays 14 and 16 are tightly secured about the micro-well assay tray(s) 39.

The invention has been described in detail including the preferred embodiments thereof. However, those skilled in the art, upon considering the present disclosure, may make modifications and improvements within the spirit and scope of the invention.

What is claimed is:

1. An active thermal control subsystem for use with at least one of polymerase chain reaction testing, chemiluminescent immuno-assay testing, and bDNA testing, the thermal control subsystem being operative to thermally-control a sample-holding device and comprising:

a fluidic circuit for transporting a heat-transferring fluid for heating and/or cooling;

a first heat spreader having a second side that is thermally coupleable to a first portion of the sample-holding device;

a first assembly including a controllable thermo-electric device and a heat removal device, the heat removal device fluidly coupled to the fluidic circuit, a first side of the thermo-electric device of the first assembly being thermally-coupled to a first side of the first heat spreader and a second side of the thermo-electric device, opposite the first side, being thermally-coupled to the heat removal device, so that said thermo-electric device distally and thermally separates said first heat spreader from said heat removal device, wherein said thermo-electric device is adapted and controllable to transfer heat from said first heat spreader to said heat removal device or from said heat removal device to said first heat spreader;

a second assembly including a controllable thermo-electric device and a heat removal device, the heat removal device fluidly coupled to the fluidic circuit, a first side of the thermo-electric device of the second assembly being thermally-coupleable to a portion of the sample-holding device and a second side of the thermo-electric device, opposite the first side, being thermally-coupled to the heat removal device so that said thermo-electric device distally and thermally separates said sample holding device from said heat removal device;

a pump that is fluidly-coupled to the fluidic circuit for circulating the heat-transferring fluid through said fluidic circuit; and a heat exchange device for removing heat from the heat-transferring fluid in the fluidic circuit.

2. The thermal control subsystem as recited in claim 1 further comprising a second heat spreader that is thermally coupled to the second assembly, wherein a first side of the second heat spreader is thermally coupled to the first side of the thermo-electric device of the second assembly and a second, opposing side of the second heat spreader is thermally-coupled to the sample-holding device, said thermo-electric device being adapted and controllable to transfer heat from said second heat spreader to said heat removal device or from said heat removal device to said second heat spreader.

3. The thermal control subsystem as recited in claim 1, wherein at least one of the heat removal devices includes a channeled plate that is fluidly-coupled to the fluidic system and the heat exchange device.

4. The thermal control subsystem as recited in claim 1, wherein current to one or both of the thermo-electric devices can be controlled to transfer heat across said thermo-electric device bi-directionally.

5. The thermal control subsystem as recited in claim 1, one or both of the first assembly and the second assembly further including at least one sub-portion for retaining the sample-holding device.

6. The thermal control subsystem as recited in claim 1, wherein said sample-holding device is a micro-well titer plate.

7. The thermal control subsystem as recited in claim 1, wherein the heat exchange device comprises:

a reservoir that is fluidly-coupled to the fluidic system for storing heat-transferring fluid;

a plurality of cooling coils through which the heat-transferring fluid can circulate; and at least one fan for forcing ambient air against and/or around the plurality of cooling coils to remove heat from the heat-transferring fluid circulating therein.

8. The thermal control subsystem as recited in claim 1, the subsystem further comprising at least one of:

a drain line that is fluidly-coupled to the fluidic system for removing heat-transferring fluid; and a controller for controlling operation of the pump, the heat exchange device, and the thermo-electric devices associated with each of the first and second assemblies.

9. A testing system that provides active thermal control of a sample-holding device, the system comprising:

an active thermal control subsystem for controlling the temperature of the sample-holding device, the thermal control subsystem comprising:

a fluidic circuit for transporting a heat-transferring fluid for heating and/or cooling, a first heat spreader having a second side that is thermally coupleable to a first portion of the sample-holding device;

a first assembly including a controllable thermo-electric device and a heat removal device, the heat removal device fluidly coupled to the fluidic circuit, a first side of the thermo-electric device of the first assembly being thermally-coupled to a first side of the first heat spreader and a second side of the thermo-electric device of the first assembly, opposite the first side, being thermally-coupled to the heat removal device, so that said thermo-electric device distally and thermally separates said first heat spreader from said heat removal device, wherein said thermo-electric device is adapted and controllable to transfer heat from said first heat spreader to said heat removal device or from said heat removal device to said first heat spreader;

a second assembly including a controllable thermo-electric device and a heat removal device, the heat removal device fluidly coupled to the fluidic circuit, a first side of the thermo-electric device of the second assembly being thermally-coupleable to a portion of the sample-holding device and a second side of the thermo-electric device of the second assembly, opposite the first side, being thermally-coupled to the heat removal device so that said thermo-electric device distally and thermally separates said sample holding device from said heat removal device;

a pump that is fluidly-coupled to the fluidic circuit for circulating the heat-transferring fluid through said fluidic circuit, and a heat exchange device for removing heat from the heat-transferring fluid in the fluidic circuit; and a controller for controlling operation of the pump, the heat exchange device, and the thermo-electric devices associated with the first and second assemblies.

10. The system as recited in claim 9, wherein the controller is operative to control current and voltage to one or both of the thermo-electric devices of the first and the second assembly to provide heat transfer across said thermo-electric device or devices bi-directionally.

11. The system as recited in claim 9, the system further comprising at least one of:

a holding device for holding and controlling a temperature of at least one reagent-containing vessel, the vessel fluidly-coupled to the fluidic system, the holding device having channels; and a drain line that is fluidly-coupled to the fluidic system for removing heat-transferring fluid therefrom.

12. The thermal control subsystem as recited in claim 1, wherein the first heat spreader is structured and arranged to maintain a temperature of the sample-holding device within approximately ±0.5° C. (1° F.) of a desired temperature.

13. The thermal control subsystem as recited in claim 1, wherein the first heat spreader is structured and arranged to control a temperature change rate for heating or cooling the sample-holding device between approximately 1° C./minute (2° F./minute) and approximately 10° C./minute (18° F./minute).

14. The thermal control subsystem as recited in claim 9, wherein the first heat spreader is structured and arranged to maintain a temperature of the sample-holding device within approximately ±0.5° C. (1° F.) of a desired temperature.

15. The thermal control subsystem as recited in claim 9, wherein the first heat spreader is structured and arranged to control a temperature change rate for heating or cooling the sample-holding device between approximately 1° C./minute (2° F./minute) and approximately 10° C./minute (18° F./minute).

* * * * *